United States Patent
Kamimura

(10) Patent No.: US 9,279,720 B2
(45) Date of Patent: Mar. 8, 2016

(54) ANALYSIS DEVICE

(75) Inventor: Ippei Kamimura, Osaka (JP)

(73) Assignee: NEC SOLUTION INNOVATORS, LTD., Tokyo (JP)

( * ) Notice: Subject to any disclaimer, the term of this patent is extended or adjusted under 35 U.S.C. 154(b) by 486 days.

(21) Appl. No.: 13/634,207

(22) PCT Filed: Feb. 21, 2011

(86) PCT No.: PCT/JP2011/053668
§ 371 (c)(1),
(2), (4) Date: Sep. 11, 2012

(87) PCT Pub. No.: WO2011/118309
PCT Pub. Date: Sep. 29, 2011

(65) Prior Publication Data
US 2013/0003054 A1    Jan. 3, 2013

(30) Foreign Application Priority Data

Mar. 24, 2010    (JP) .................................. 2010-067808

(51) Int. Cl.
*G01J 3/02*    (2006.01)
*G01J 3/42*    (2006.01)
(Continued)

(52) U.S. Cl.
CPC ..... *G01J 3/02* (2013.01); *G01J 3/10* (2013.01); *G01J 3/18* (2013.01); *G01J 3/36* (2013.01); *G01J 3/42* (2013.01); *G01N 21/255* (2013.01);
(Continued)

(58) Field of Classification Search
CPC ............ G02B 5/204; G01J 3/51; G01J 3/513; G01J 3/02

USPC ........................................................ 359/360
See application file for complete search history.

(56) References Cited

U.S. PATENT DOCUMENTS 3,277,773 A * 10/1966 White ............................ 356/323
3,892,492 A *  7/1975 Eichenberger ................ 356/434
(Continued)

FOREIGN PATENT DOCUMENTS

JP        04-313007 A    11/1992
JP        06-213804 A     8/1994
(Continued)

OTHER PUBLICATIONS

International Search Report in PCT/JP2011/053668 dated May 24, 2011 (English Translation Thereof).
(Continued)

*Primary Examiner* — Michael A Lyons
*Assistant Examiner* — Dominic J Bologna
(74) *Attorney, Agent, or Firm* — McGinn IP Law Group, PLLC.

(57) ABSTRACT

An analysis device for analyzing components contained in an object includes a light emitting unit that irradiates the object with light, a transmissive spectral filter, a light detector including a plurality of light receiving elements, an analysis unit. The spectral filter includes a substrate having light transmissivity and being disposed on a light path of the light after being reflected by the object or the light after passing through the object, a plurality of raised portions formed with a metal material on one surface of the substrate, and a metal oxide film including a metal oxide material having a higher refractive index than the metal material, so as to cover the plurality of raised portions and the one surface of the substrate.

14 Claims, 8 Drawing Sheets

(51) Int. Cl.
*G01N 21/25* (2006.01)
*G02B 5/20* (2006.01)
*G01N 21/31* (2006.01)
*G01J 3/10* (2006.01)
*G01J 3/18* (2006.01)
*G01J 3/36* (2006.01)
*G02B 5/18* (2006.01)
*G01N 21/27* (2006.01)
*G01N 21/35* (2014.01)
*G01N 21/3563* (2014.01)
*G01N 21/3577* (2014.01)

(52) U.S. Cl.
CPC ............. G01N 21/31 (2013.01); G02B 5/1809 (2013.01); G02B 5/203 (2013.01); *G01N 21/274* (2013.01); *G01N 21/35* (2013.01); *G01N 21/3563* (2013.01); *G01N 21/3577* (2013.01); *G01N 2021/3166* (2013.01); *G01N 2021/3177* (2013.01); *G02B 5/201* (2013.01)

(56) References Cited

U.S. PATENT DOCUMENTS

| | | | | |
|---|---|---|---|---|
| 4,629,322 | A * | 12/1986 | Pollard | 356/300 |
| 4,750,837 | A * | 6/1988 | Gifford et al. | 356/417 |
| 5,272,345 | A * | 12/1993 | Durham et al. | 250/373 |
| 5,726,805 | A | 3/1998 | Kaushik et al. | |
| 6,721,054 | B1 * | 4/2004 | Spooner | 356/445 |
| 2002/0135869 | A1 * | 9/2002 | Banish et al. | 359/350 |
| 2003/0049858 | A1 * | 3/2003 | Golden et al. | 436/171 |
| 2006/0006778 | A1 | 1/2006 | Lee et al. | |
| 2006/0273245 | A1 | 12/2006 | Kim et al. | |
| 2008/0135739 | A1 | 6/2008 | Kim et al. | |
| 2009/0073434 | A1 | 3/2009 | Kim et al. | |
| 2009/0128895 | A1 * | 5/2009 | Seo et al. | 359/360 |
| 2010/0059663 | A1 | 3/2010 | Desieres | |
| 2010/0220377 | A1 * | 9/2010 | Yamada et al. | 359/241 |
| 2010/0290051 | A1 * | 11/2010 | Yamada et al. | 356/445 |
| 2011/0043813 | A1 * | 2/2011 | Yamada | 356/447 |

FOREIGN PATENT DOCUMENTS

| | | |
|---|---|---|
| JP | 2000-356591 A | 12/2000 |
| JP | 2002-196123 A | 7/2002 |
| JP | 2005-331581 A | 12/2005 |
| JP | 2006-012826 A | 1/2006 |
| JP | 2006-170669 A | 6/2006 |
| JP | 2007-501391 A | 1/2007 |
| JP | 2007-255969 A | 10/2007 |
| JP | 2009-534700 A | 9/2009 |
| JP | 2010-051589 A | 3/2010 |
| WO | WO 2009093453 A1 * | 7/2009 |

OTHER PUBLICATIONS

'Bunkogakuteki Seishitsu o Shu toshita Kiso Bussei Zuhyo', 1$^{st}$ Edition, Kyoritsu Shuppan Co., Ltd., May 15, 1972, pp. 202, 471, 500, NBN: JP-6900569.

European Search Report dated Feb. 12, 2015.

* cited by examiner (a) Absorbance

Glucose concentration (b) Absorbance

Sucrose concentration (c) Absorbance

Fructose concentration

ANALYSIS DEVICE

TECHNICAL FIELD

The present invention relates to an analysis device for optically analyzing components contained in an object.

BACKGROUND ART

Conventionally, an optical analysis method has been proposed in order to perform non-destructive analysis of components contained in an object. With the optical analysis method, first the object is irradiated with light. Next, a spectral filter is used to extract light of a wavelength corresponding to a target component from transmitted light that has passed through the object or reflected light that has been reflected by the object, and the extracted light is received by a light receiving element. Absorbance is then derived, based on an output signal from the light receiving element, and the percentage of target component is furthermore calculated from the absorbance (e.g., see Patent Literatures 1 and 2).

Specifically, Patent Literature 1 discloses an analysis device that performs optical analysis with glucose contained in fruit and vegetables as the target component. With the analysis device disclosed in Patent Literature 1, since the target component is glucose, light containing wavelengths in the near-infrared region is irradiated from a light source. As for the spectral filter, a reflective spectral filter using a diffraction grating is used. This spectral filter is formed so that only light of wavelengths in a range of 700 nm to 1000 nm is guided to the light receiving element.

Patent Literature 2 also discloses an analysis device that takes glucose contained in fruit and vegetables as the target component. With the analysis device disclosed in Patent Literature 2, however, a plurality of transmissive spectral filters that transmit only light of set wavelengths are used, different from the analysis device disclosed in Patent Literature 1. The spectral filters are disposed in the same plane within the beam irradiation range. As a result of this configuration, only light from the object being measured that conforms to the set wavelength of one of the spectral filters passes through the spectral filters and is received by the light receiving element.

Incidentally, with the abovementioned optical analysis method, in the case where the target component differs, the wavelengths (selected wavelengths) of light to be extracted using a spectral filter will also differ. Consequently, with the analysis devices disclosed in Patent Literature 1 and Patent Literature 2, the spectral filter needs to be exchanged in the case of targeting components other than glucose, making it practically impossible to target components other than glucose.

On the other hand, Patent Literature 3 discloses a reflective spectral filter that enables the selected wavelength to be changed. The spectral filter disclosed in Patent Literature 3 is provided with a resonance grating, a substrate disposed such that a gap is formed therebetween, and a configuration for applying a voltage between the resonance grating and the substrate. When the magnitude of the voltage applied between the resonance grating and the substrate is changed in this spectral filter, the distance therebetween changes, resulting in reflectance relative to incident light also changing. If the spectral filter disclosed in Patent Literature 3 is used, the selected wavelength can thus be changed, and an analysis device capable of handling a wide variety of target components can conceivably be obtained.

CITATION LIST

Patent Literatures

Patent Literature 1: JP 06-213804A
Patent Literature 2: JP 2000-356591A
Patent Literature 3: JP 2005-331581A

DISCLOSURE OF THE INVENTION

Problem to be Solved by the Invention

However, since the spectral filter disclosed in Patent Literature 3 is a reflective spectral filter, the light path is complex in the case where an analysis device is constituted using this spectral filter. Also, more space is required to install the spectral filter disclosed in Patent Literature 3 than that required for other spectral filters. From these reasons, in the case where the spectral filter disclosed in Patent Literature 3 is used in an analysis device, the problem of the analysis device increasing in size arises.

An exemplary object of the present invention is to solve the above problems, and to provide an analysis device capable of handling analysis of a wide variety of components, while suppressing an increase in device size.

Means for Solving the Problem

In order to attain the above object, an analysis device according to one aspect of the present invention is an analysis device for analyzing components contained in an object, the analysis device including a light emitting unit that irradiates the object with light, a transmissive spectral filter, a light detector having a plurality of light receiving elements, and an analysis unit, the spectral filter including a substrate having light transmissivity and being disposed on a light path of the light after being reflected by the object or the light after passing through the object, a plurality of raised portions formed with a metal material on one surface of the substrate, and a metal oxide film formed using a metal oxide material having a higher refractive index than the metal material, so as to cover the plurality of raised portions and the one surface of the substrate, and the plurality of raised portions being disposed such that the metal oxide film existing between adjacent raised portions serves as a diffraction grating and the raised portions serve as a waveguide, at least one of a grating pitch of the diffraction grating, a height of the raised portions, and a thickness of the metal oxide film being set to a different value for each portion of the spectral filter, such that a wavelength of light that passes through the spectral filter changes for each of the portions, the light detector being disposed such that each of the plurality of light receiving elements receives light that passes through the spectral filter, and the analysis unit acquiring a spectrum of the object from output signals respectively output by the plurality of light receiving elements.

Effects of the Invention

As a result of the above features, an analysis device of the present invention is able to handle analysis of a wide variety of components, while suppressing an increase in device size.

BEST MODE FOR CARRYING OUT THE INVENTION

Embodiment 1

Figure 1:
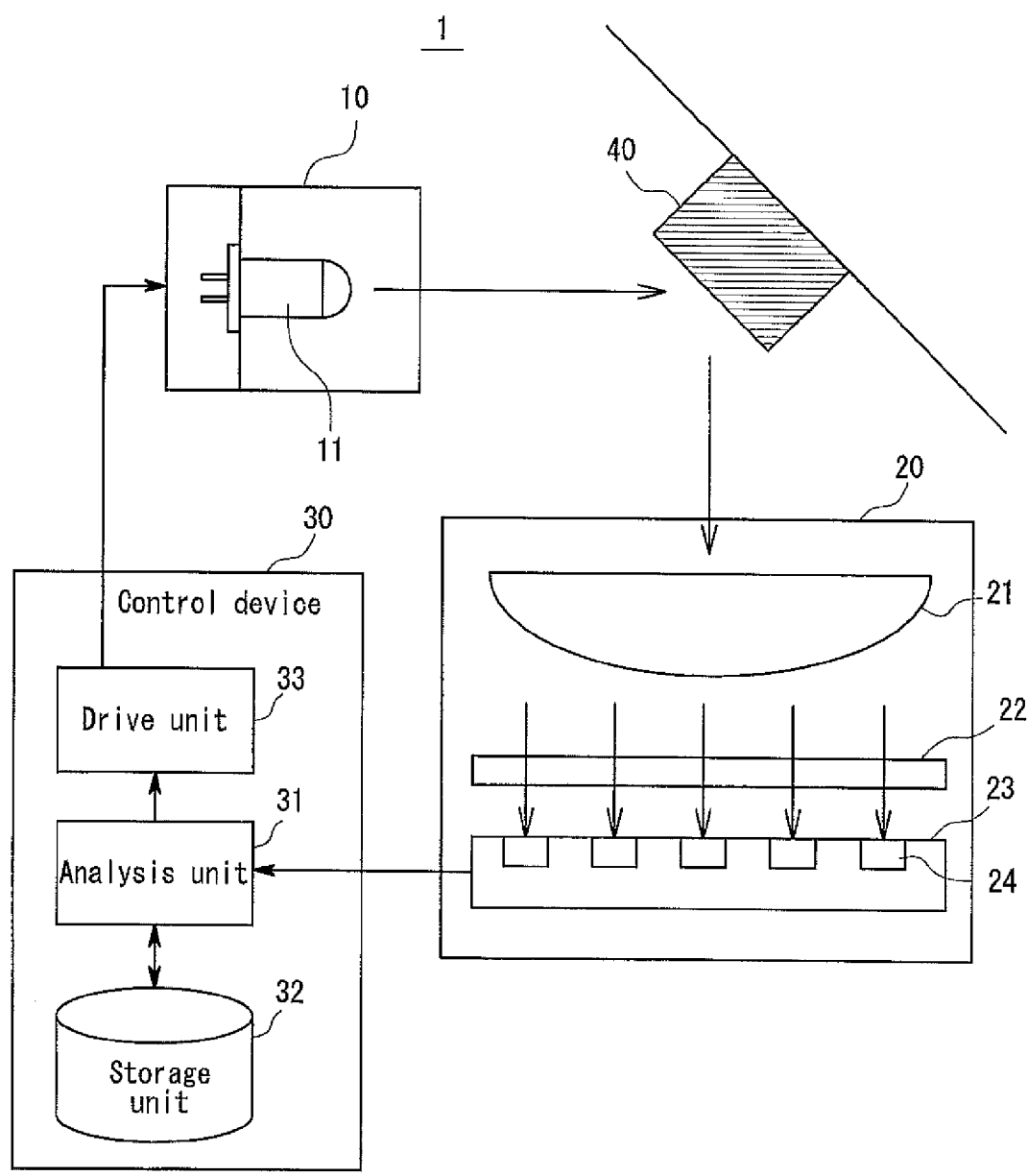
FIG. 1 is a configuration diagram showing a schematic configuration of an analysis device in Embodiment 1 of the present invention.
Figure 2:
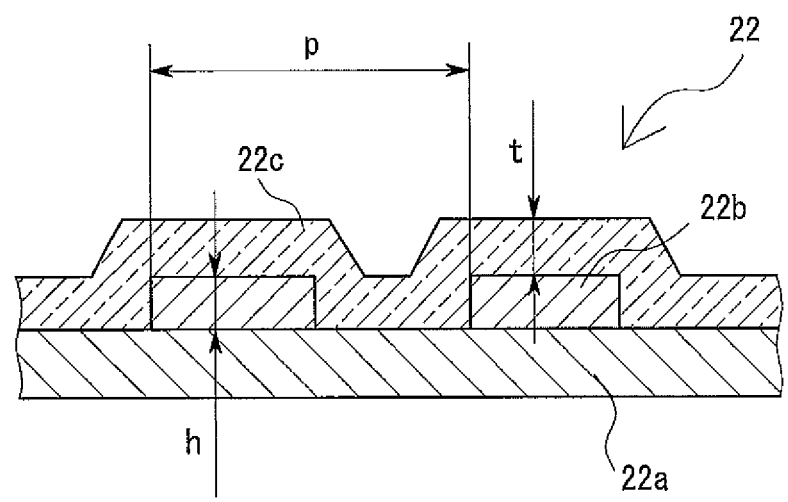
FIG. 2 is a partially enlarged cross-sectional view showing a configuration of a spectral filter shown in FIG. 1.

Hereinafter, an analysis device in Embodiment 1 of the present invention will be described, with reference to FIG. 1 to FIG. 5. Initially, the configuration of an analysis device 1 in the present Embodiment 1 will be described, using FIG. 1 and FIG. 2. FIG. 1 is a configuration diagram showing a schematic configuration of the analysis device in Embodiment 1 of the present invention. FIG. 2 is a partially enlarged cross-sectional view showing the configuration of a spectral filter shown in FIG. 1.

As shown in FIG. 1, the analysis device 1 is a device that analyzes components contained in an object 40. The analysis device 1 is provided with a light emitting unit 10 that irradiates the object 40 with light, a transmissive spectral filter 22, a light detector 23 having a plurality of light receiving elements 24, and an analysis unit 31. The spectral filter 22 is disposed on the light path of light reflected by the object 40, and is configured so that the wavelength of light that passes through the spectral filter 22 changes for every portion thereof. Also, the spectral filter 22 may, different from the example in FIG. 1, be disposed on the light path of light that has passed through the object 40.

In the present Embodiment 1, the spectral filter 22 together with the light detector 23 constitutes a sensor unit 20 that detects light from the object 40. Also, the sensor unit 20 is provided with a lens 21. The lens 21 is used in order to condense light reflected by the object 40 and efficiently guide this light to the spectral filter 22. Note that although space exists between the spectral filter 22 and the light detector 23 in FIG. 1, this is for illustrating the configuration, and in practice the spectral filter 22 and the light detector 23 are in close contact, without space therebetween.

Here, the configuration and functions of the spectral filter 22 will be described based on FIG. 2. As shown in FIG. 2, the spectral filter 22 is provided with a substrate 22a having light transmissivity, a plurality of raised portions 22b formed on one surface of the substrate 22a, and a metal oxide film 22c covering the one surface of the substrate 22a as well as the plurality of raised portions 22b. Of these, the raised portions 22b are formed with a metal material, and the metal oxide film 22c is formed using a metal oxide material having a higher refractive index than the metal material.

Also, the plurality of raised portions 22b are disposed so that the metal oxide film 22c existing between adjacent raised portions serves as a diffraction grating. Specifically, the raised portions 22b are each formed in the shape of a rectangular column, and are furthermore disposed in a matrix. In order for the metal oxide film 22c to function as a diffraction grating, a grating pitch p of the diffraction grating is set for each portion having a different wavelength of transmitted light, so as to be shorter than the wavelength of light that is required to pass through that portion.

Because the raised portions 22b serve as a sub wavelength grating and function as a waveguide as a result of such a configuration, light that is incident on the raised portions 22b from the metal oxide film 22c side propagates inside the raised portions 22b as an evanescent wave. Light that is incident on the raised portions 22b passes through the raised portions 22b and the substrate 22a or is reflected by the substrate 22a after passing through the raised portions 22b, according to the wavelength of the light. Specifically, the wavelength of transmitted light tends to lengthen if a height h of the raised portions 22b is raised. Similarly, the wavelength of transmitted light tends to lengthen in the case where the grating pitch p of the diffraction grating is widened or the refractive index of the substrate 22a is increased. Note that, in practice, it is difficult to change the refractive index of each member on a portion-by-portion basis.

Accordingly, in the spectral filter 22, in order to change the wavelength of light that passes through the spectral filter 22 on a portion-by-portion basis, at least one of the grating pitch p of the diffraction grating, the height h of the raised portions 22b and a thickness t of the metal oxide film 22c is set to a different value for each portion. In other words, the spectral filter 22 is formed so that the wavelength of transmitted light differs for each portion thereof. Note that transmitted light, in practice, has a wavelength in the narrowband, and the wavelength of transmitted light is set with regard to the center wavelength in the narrowband. Also, the grating pitch p of the diffraction grating is, substantively, the distance from the lateral face on one side of one raised portion 22b to the lateral face on the same side of an adjacent raised portion 22b, as shown in FIG. 2.

In the present Embodiment 1, the material of the substrate 22a, the raised portions 22b and the metal oxide film 22c can be set as appropriate so that light of the target wavelength can pass through easily. For example, taking the case of transmitted light being light in the infrared region as an example, the material of the substrate 22a may be silicon oxide ($SiO_2$). In this case, the substrate 22a is a so-called quartz substrate. Also, gold (Au) or an alloy containing gold (Au) may be used as the metal material forming the raised portions 22b. Furthermore, titanium oxide ($TiO_2$) may be used as the material of the metal oxide film 22c.

Here, an example in which the center wavelength of transmitted light is set to 1.48 μm, for example, in the case where transmitted light is light in the infrared region will be described. The refractive index of titanium oxide forming the metal oxide film 22c is "1.904", the refractive index of silicon oxide forming the substrate 22a is "1.465" and the reflectance of gold is "0.944". Also, the height h of the raised portions 22b is set to "62 μm". Although countless values exist for the refractive index and extinction coefficient of gold, in the above example the refractive index and extinction coefficient of gold are "0.50" and "7.1", respectively. In such an example, the grating pitch p of the diffraction grating and the thickness t of the metal oxide film 22c need only be set to "1064.7 μm" and "134 μm", respectively.

Also, as shown in FIG. 1, the light detector 23 is disposed so that each light receiving element 24 receives light that passes through the spectral filter 22. Therefore, because light that has passed through the spectral filter 22 is received by a different light receiving element 24 in each portion of the spectral filter 22, the output signal of each light receiving element 24 will indicate the intensity of light of the set wavelength of the corresponding portion as a result of the functioning of the abovementioned spectral filter 22. Accordingly, the analysis unit 31 is able to acquire the spectrum of the object 40 from the output signals of the light receiving elements 24.

In the example of FIG. 1, a solid-state imaging device having a semiconductor substrate on which a plurality of photo-diodes are formed in a matrix is used as the light detector 23. Also, in FIG. 1, for descriptive purposes, the light detector 23 is shown in cross-section. Note that hatching is omitted in the cross-section.

In this way, with the analysis device 1 in the present Embodiment 1, since a reflective spectral filter such as the spectral filter disclosed in Patent Literature 3 is not used, the light path can be simplified as shown in FIG. 1, and an increase in device size is suppressed. Also, since a spectrum can be acquired without being limited by the type of object 40, the analysis of other types of components can be handled with a single device.

Also, in the present Embodiment 1, the analysis unit 31 is able to identify a component contained in the object 40 from the acquired spectrum. Furthermore, the analysis unit 31 is able to select a calibration curve corresponding to the identified component from a plurality of calibration curves prepared in advance, and calculate the content of the component targeted for analysis using the selected calibration curve. Specifically, the analysis unit 31 calculates the content of the component targeted for analysis, by deriving absorbance from the acquired spectrum and applying the derived absorbance to the selected calibration curve.

In the present Embodiment 1, the plurality of calibration curves are stored in a storage unit 32. The storage unit 32 together with the analysis unit 31 constitutes a control device 30. The control device 30 is, furthermore, also provided with a drive unit 33. The drive unit 33 drives the light emitting unit 10 and controls on/off of a light source 11, according to instructions from the analysis unit 31. A specific example of the control device 30 is a microcomputer.

In the present Embodiment 1, the light source need only be capable of irradiating light of wavelengths in a required range, and is not particularly limited. The light source 11 is, for example, an LED or a halogen lamp. In the example of FIG. 1, the light source 11 is an LED capable of irradiating light in the infrared region. Also, the range of wavelengths of emitted light required of the light source 11 is set as appropriate according to the type of object that is envisioned.

Figure 3:
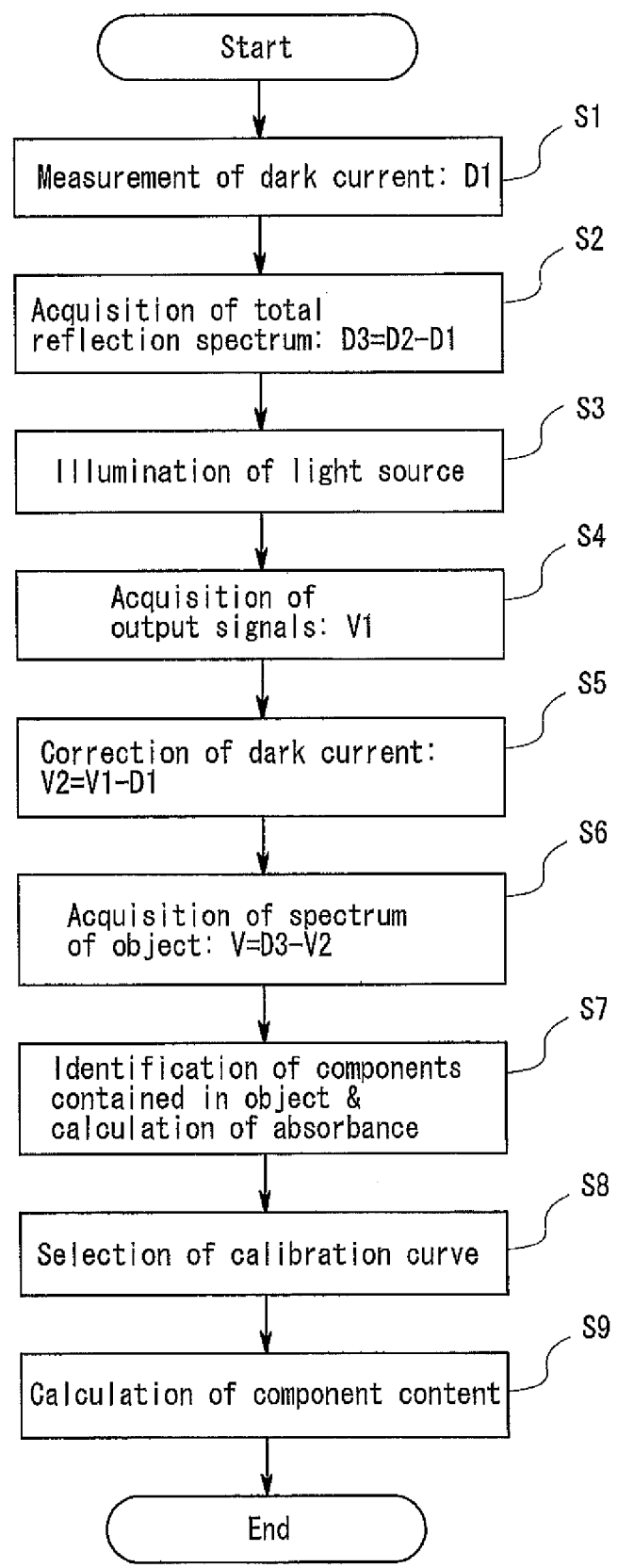
FIG. 3 is a flowchart showing operations of the analysis device in Embodiment 1 of the present invention.
Figure 4:
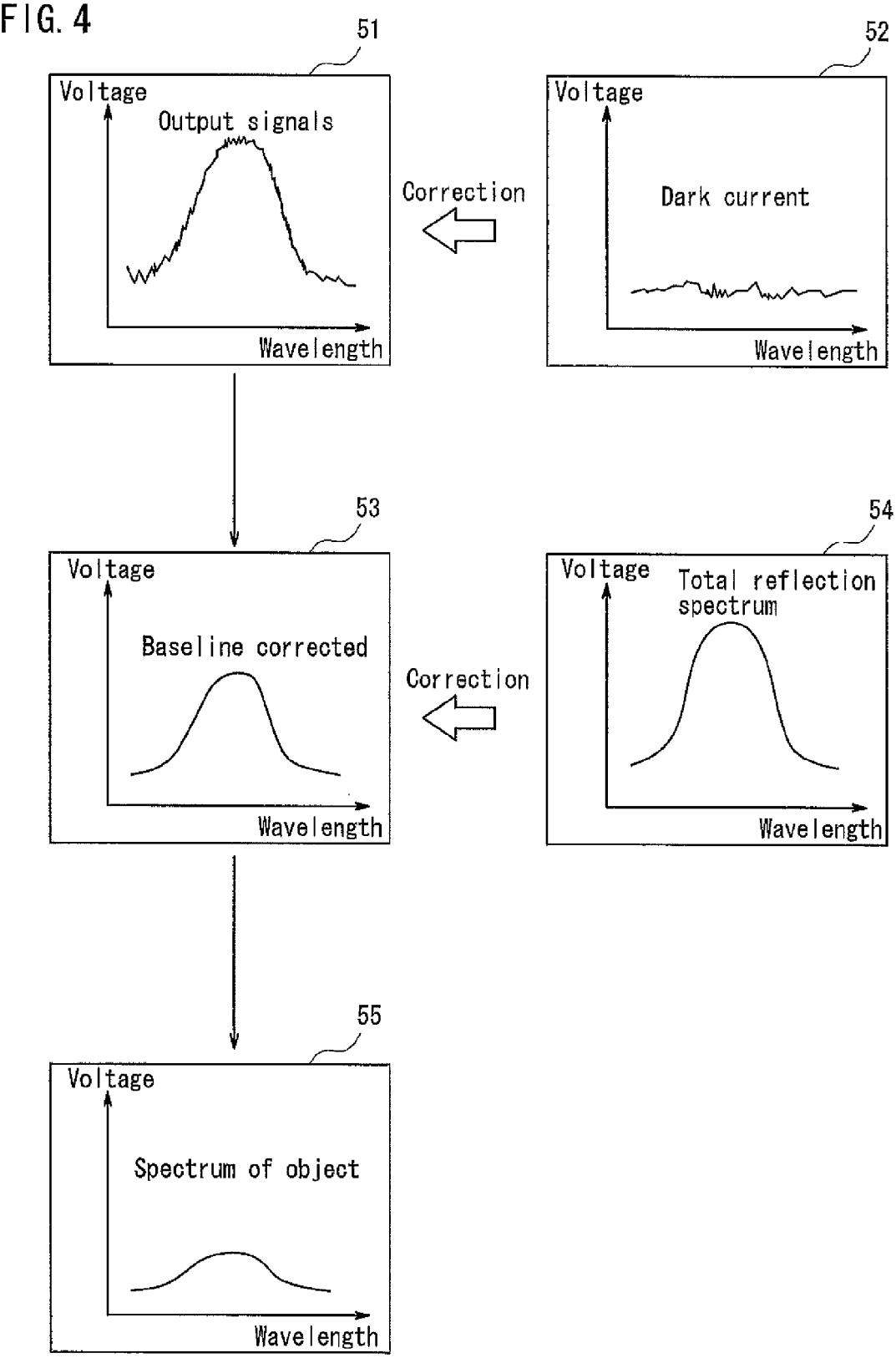
FIG. 4 is an illustrative diagram illustrating processing executed by the analysis device in Embodiment 1 of the present invention.
Figure 5:
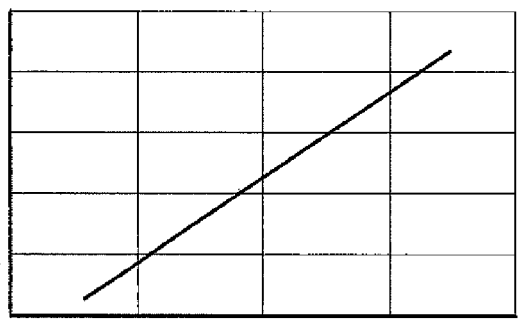
FIG. 5 shows exemplary calibration curves that are used in Embodiment 1 of the present invention, with FIG. 5(a) to FIG. 5(c) each showing a different calibration curve.
Figure 5:
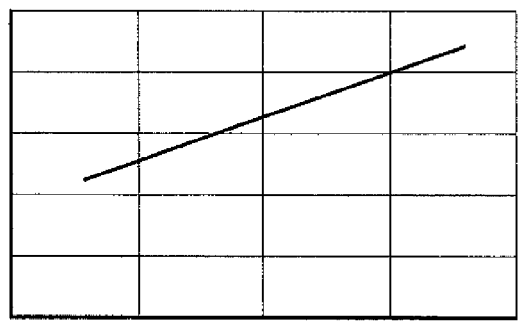
Figure 5:
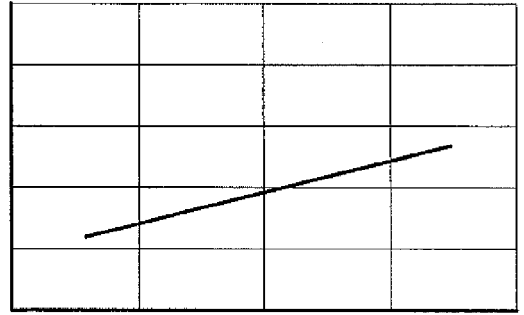

Next, operations of the analysis device 1 in the present Embodiment 1 will be described using FIG. 3 to FIG. 5. FIG. 3 is a flowchart showing operations of the analysis device in Embodiment 1 of the present invention. FIG. 4 is an illustrative diagram illustrating processing executed by the analysis device in Embodiment 1 of the present invention. FIG. 5 shows exemplary calibration curves used in Embodiment 1 of the present invention, with FIG. 5(a) to FIG. 5(c) each showing a different calibration curve. Also, in the following description, FIG. 1 and FIG. 2 are referred to as appropriate.

As shown in FIG. 3, initially, the analysis unit 31 measures dark current output by each light receiving element 24 of the light detector 23 (step S1). Specifically, the analysis unit 31 measures the output values of output signals output by the light receiving elements 24 of the light detector 23, in a state where the drive unit 33 has been caused to turn off the light source 11. Note that the output values in this case are the voltage values of signals output at the time of dark current generation.

Here, the output values (voltages) of the output signals of the light receiving elements 24 at the time of dark current generation are given as $D1_1$-$D1_n$. n denotes the number of light receiving elements. The analysis unit 31 is also able to derive an average value Dm1 of the output values $D1_1$-$D1_n$ of the output signals at the time of dark current generation, and use the average value Dm1 in subsequent computations.

In FIG. 4, a graph 52 shows exemplary output signals at the time of dark current generation in step S1. Since the wavelength of received light differs for each light receiving element 24, when the output values $D1_1$-$D1_n$ of the output signals obtained at step S1 are plotted, the graph 52 whose horizontal axis is wavelength and whose vertical axis is voltage will be obtained, as shown in FIG. 4.

Next, the analysis unit 31 causes the drive unit 33 to turn on the light source 11, and acquires a total reflection spectrum (step S2). Specifically, the analysis unit 31 causes the drive unit 33 to turn on the light source 11, and measures the output values of the output signals output by the light receiving elements 24 at that time, under conditions where a total reflection mirror is disposed instead of the object 40. The output values of the output signals at this time are given as $D2_1$-$D2_n$.

The analysis unit 31 then respectively subtracts the output values $D1_1$-$D1_n$ of the output signals at the time of dark current generation obtained at step S1 from the obtained output values $D2_1$-$D2_n$ of the output signals of the light receiving elements 24, and derives a total reflection spectrum from the obtained output values. The following Equation 1 is established, where $D3_1$-$D3_n$ are the output values constituting the total reflection spectrum. Also, in Equation 1, the analysis unit 31 may subtract the average value Dm1 of the output values $D1_1$-$D1_n$, instead of the output value $D1_k$.

$$D3_k = D2_k D1_k \qquad \text{Equation 1}$$

"k" denotes that the value was obtained from the k-th light receiving element, where $1 \leq k \leq n$. In FIG. 4, a graph 54 is obtained by plotting the output values $D3_1$-$D3_n$ constituting the total reflection spectrum, and shows an exemplary total reflection spectrum obtained at step S2.

Note that in the present Embodiment 1, step S1 may be executed after the measurement of output values in step S2, and thereafter the calculation of output values constituting the total reflection spectrum may be executed. Also, step S1 and step S2 do not need to be executed continuously with step S3 which will be described below. Furthermore, after steps S1 and S2 have been executed once, the steps from step S3 onward may be executed repeatedly. That is, steps S1 and S2 need only be executed once before execution of step S3. Also, there may be a time lag between execution of steps S1 and S2 and execution of steps S3 onward.

Next, after the end of step S2, the analysis unit 31 causes the drive unit 33 to turn on the light source 11 (step S3). As a result of step S3, the light emitted from the light source 11 is incident on the object 40, and, after being reflected by the object 40, is incident on the sensor unit 20. Thereafter, the analysis unit 31 measures the output values of the output signals output by the light receiving elements 24 (step S4).

Here, the output values (voltages) of the output signals of the light receiving elements 24 at the time of the execution of step S4 are given as $V1_1$-$V1_n$. Also, in FIG. 4, a graph 51 is obtained by plotting the output values $V1_1$-$V1_n$ of the output signals measured at step S4, and shows exemplary output signals output by the light receiving elements 24 in step S4.

Also, in the present Embodiment 1, illumination of the light source 11 in steps S2 and S3 may be performed intermittently. That is, the drive unit 33 is able to cause the light source 11 to perform pulse illumination. This is because the amount of light may fall gradually over time when the light source 11 is caused to continuously emit light, resulting in an error in the absorbance calculation in step S5 which will be discussed later.

When the light source 11 performs pulse illumination, the analysis unit 31 measures the output values of the output signals from the light receiving elements 24 for the number of illuminations. In this case, the analysis unit 31 is able to calculate the average value of the output values for each light receiving element, and use the calculated average values in the processing of steps S4 onward.

For example, in the case where, in step S2, the output values $D2_1$-$D2_n$ are obtained a plurality of times as a result of pulse illumination, the analysis unit 31 is able to calculate average values $Dm2_1$-$Dn2_n$, respectively, for the output values, and use those values. Also, in the case where output values $V1_1$-$V1_n$ are obtained a plurality of times in step S4 as a result of the pulse illumination in step S3, the analysis unit 31 is able to calculate average values $Vm1_1$-$Vm1_n$, respectively, for the output values, and use those values.

Next, the analysis unit 31 performs dark current correction on the output signals obtained at step S4 (step S5). Specifically, at step S4, the analysis unit 31 subtracts the output values $D1_1$-$D1_n$, of dark current (see graph 52 in FIG. 4) from the output values $V1_1$-$V1_n$ of the output signals obtained at step S3 (see graph 51 in FIG. 4) and performs baseline correction, using the following Equation 2. In the following Equation 2, $V2_k$ denotes the output value after correction. In the following Equation 2, the analysis unit 31 may similarly subtract the average value Dm1 of the output values $D1_1$-$D1_n$, instead of the output value $D1_k$.

$$V2_k = V1_k - D1_k \qquad \text{Equation 2}$$

Also, in FIG. 4, a graph 53 is obtained by plotting the output values $V2_1$-$V2_n$ after correction, and shows exemplary baseline-corrected output signals obtained at step S5.

Next, the analysis unit 31 acquires the spectrum of the object 40, using the baseline-corrected output values and the output values of the total reflection spectrum (see graph 54 in FIG. 4) (step S6). Specifically, the analysis unit 31 calculates the difference of the baseline-corrected output values and the output values of the total reflection spectrum (see graph 54 in FIG. 4), using the following Equation 3. The calculated difference is equivalent to the spectrum of the object 40. In the following Equation 3, $V_k$ denotes the difference value.

$$V_k = D3_k - V2_k \qquad \text{Equation 3}$$

In FIG. 4, a graph 55 is obtained by plotting the calculated difference values $V_1$-$V_n$, and shows an exemplary spectrum (difference) of the object 40. Also, in the present Embodiment 1, a spectrum in the infrared region is obtained, given that the light source 11 irradiates light in the infrared region, as mentioned above.

Next, the analysis unit 31, by, for example, specifying the peak wavelength that appears based on the spectrum obtained at step S4, identifies components contained in the object 40, and, furthermore, calculates absorbance from the value of the peak wavelength (step S7).

Specifically, in the present Embodiment 1, a peak occurrence pattern is stored in the storage unit 32 in advance, for each component that is envisioned. In step S7, the analysis unit 31 applies the specified peak wavelength to the stored occurrence patterns, and identifies components contained in the object 40 from the result thereof. Also, given that the spectrum obtained in the present Embodiment 1 is a spectrum in the infrared region, as mentioned above, components that are identified include glucose, sucrose, fructose, citrate and water.

Also, in step S7, the analysis unit 31 calculates an absorbance $A_\lambda$ from the following Equation 4. Note that in the following Equation 4, j represents the light receiving element that outputs the peak value. Also, $1 \leq j \leq n$.

$$A_\lambda = -\log_{10}(V2_j/D3_j) \qquad \text{Equation 4}$$

Next, the analysis unit 31 accesses the storage unit 32, and selects calibration curves (see diagrams 5(a)-(c)) corresponding to the object 40, based on the identification result at step S7 (step S8). For example, if the object 40 is blood and the identified component is glucose (blood sugar), the analysis unit 31 selects the calibration curve shown in FIG. 5(a). Also, if the object 40 is a fruit such as a mandarin or a strawberry, and the identified components are glucose, sucrose and fructose, the analysis unit 31 selects the calibration curves shown in FIGS. 5(a)-(c).

Thereafter, the analysis unit 31 calculates the content (concentration) of the components contained in the object 40 by applying the absorbance $A_\lambda$ calculated at step S7 to the calibration curves selected at step S8 (step S9). In the case where the object 40 is blood, for example, the analysis unit 40 calculates glucose concentration (blood sugar level). Also, in the case where the object 40 is a fruit such as a mandarin or a strawberry, for example, the analysis unit 31 calculates glucose concentration, sucrose concentration, and fructose concentration. After the end of step S7, the analysis unit 31 outputs the result and ends the processing.

As mentioned above, according to the analysis device 1 of the present Embodiment 1, it is possible to specify components contained in an object 40 and suitable calibration curves, and to perform component analysis of various objects. Also, since the optical system required in order to perform component analysis has a simple configuration, an increase in device size is suppressed.

Note that in the present Embodiment 1, since the spectral filter 22 is configured so that the wavelength of incident light differs for each light receiving element, the analysis unit 31 performs arithmetic operations on output values for each light receiving element. However, the present invention is not limited to this example. For example, the spectral filter 22 may be configured so that the wavelength of incident light differs for each group constituted by two or more light receiving elements. In this case, the analysis unit 31 calculates the average value of output values for each group, and performs the abovementioned arithmetic operations using the obtained average values.

Also, in the present Embodiment 1, the type of object 40 is not particularly limited, and, in addition to the abovementioned blood and fruit, specifically includes vegetables, foodstuffs, chemical substances, and various body fluids extracted from living organisms.

Embodiment 2

Figure 6:
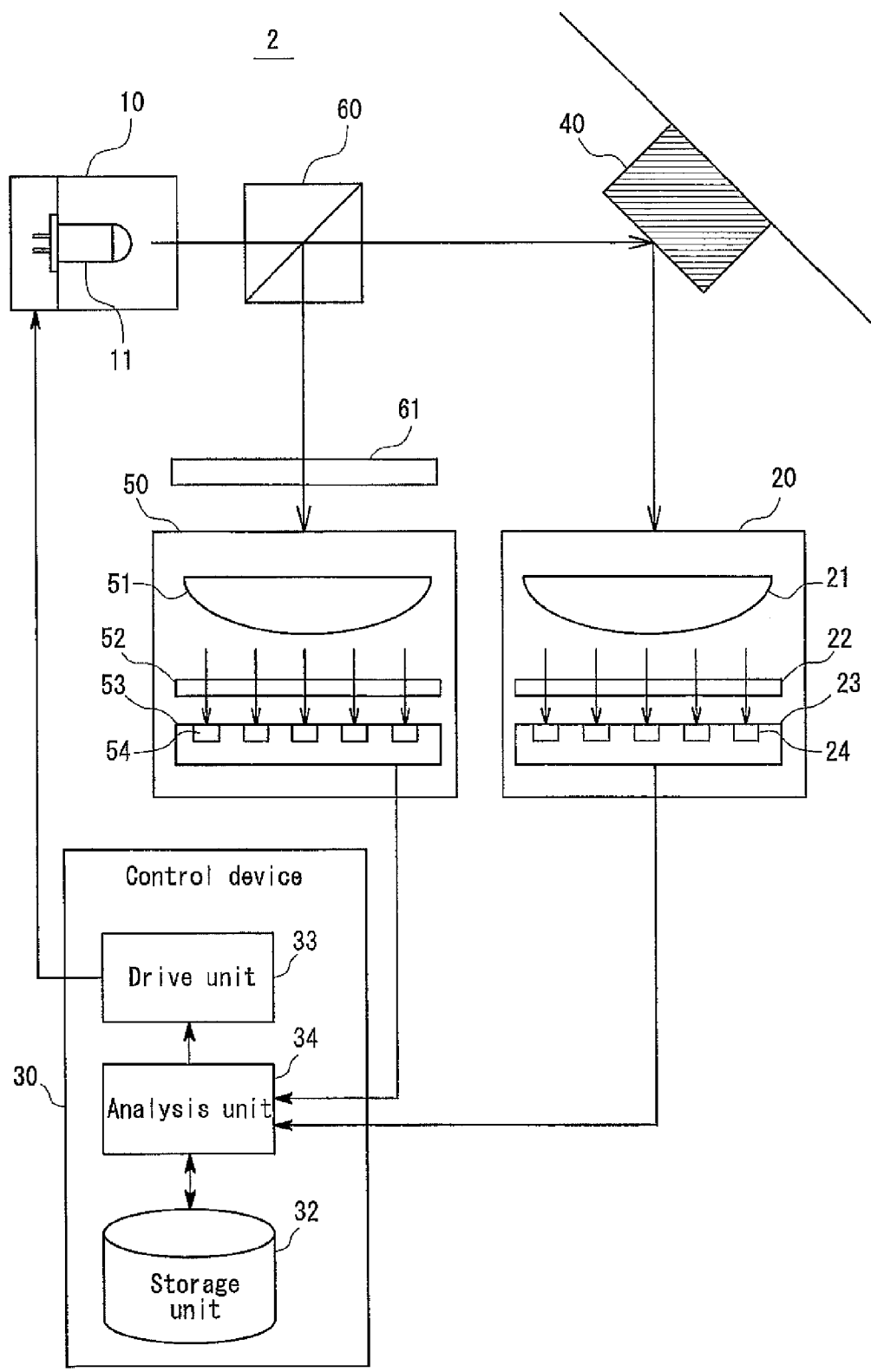
FIG. 6 is a configuration diagram showing a schematic configuration of an analysis device in Embodiment 2 of the present invention.

Next, an analysis device in Embodiment 2 of the present invention will be described, with reference to FIG. 6 and FIG. 7. Initially, the configuration of an analysis device 2 in the present Embodiment 2 will be described using FIG. 6. FIG. 6 is a configuration diagram showing a schematic configuration of the analysis device in Embodiment 2 of the present invention.

As shown in FIG. 6, in the present Embodiment 2, the analysis device 2, different from the analysis device 1 in Embodiment 1 shown in FIG. 1, is provided with a reference sensor unit 50 in addition to the sensor unit (hereinafter, "main sensor unit") 20.

The analysis device 2, different from the analysis device 1, is also provided also with a beam splitter 60 that splits light irradiated from the light emitting unit 10 and a neutral density (ND) filter 61. Furthermore, as a result of such differences in configuration, an analysis unit 34 also executes processing that is not executed by the analysis unit 31 of the analysis device 1. Note that except for the abovementioned differences, the analysis device 2 is similar to the analysis device 1 in Embodiment 1 shown in FIG. 1. Hereinafter, the description will focus on the differences from Embodiment 1.

The beam splitter 60 is disposed between the light emitting unit 10 and the object 40, and splits light irradiated by the light emitting unit 10 in two prior to the light being incident on the object 40. One beam of the split light is incident on the object 40, where it is reflected and then received by the main sensor unit 20. The other beam is received by the reference sensor unit 50 via the ND filter 61, without being incident on the object 40.

The reference sensor unit 50 is provided with a lens 51, a spectral filter 52 and a light detector 53 having a plurality of light receiving elements 54, and is configured similarly to the main sensor unit 20. That is, the spectral filter 52 is the same as the spectral filter 22, and the light detector 53 is the same as the light detector 23. Also, the lens 51 is the same as the lens 21. Also, the ND filter 61 is configured so that the amount of light after passing through the ND filter 61 is the same as the amount of light after being reflected by the object 40.

Note that although space exists between the spectral filter 22 and the light detector 23 and between the spectral filter 52 and the light detector 53 in FIG. 6, this is for illustrating the configuration. In practice, the spectral filter 22 is in close contact with the light detector 23 and the spectral filter 52 is in close contact with the light detector 53, without any space existing therebetween.

In the analysis device 2, two sensor units, namely, the main sensor unit 20 and the reference sensor unit 50, are thus used. Therefore, in the present Embodiment 2, different from Embodiment 1, a total reflection spectrum does not need to be acquired. Also, because the degree of deterioration in the amount of light in the case of the light source 11 being caused to continuously emit light can be detected by the reference sensor unit, the light source 11 is caused to continuously emit light in the present Embodiment 2.

Next, operations of the analysis device 2 in the present Embodiment 2 will be described using FIG. 7. FIG. 7 is a flowchart showing operations of the analysis device in Embodiment 2 of the present invention. Also, in the following description, FIG. 6 is referred to as appropriate.

Figure 7:
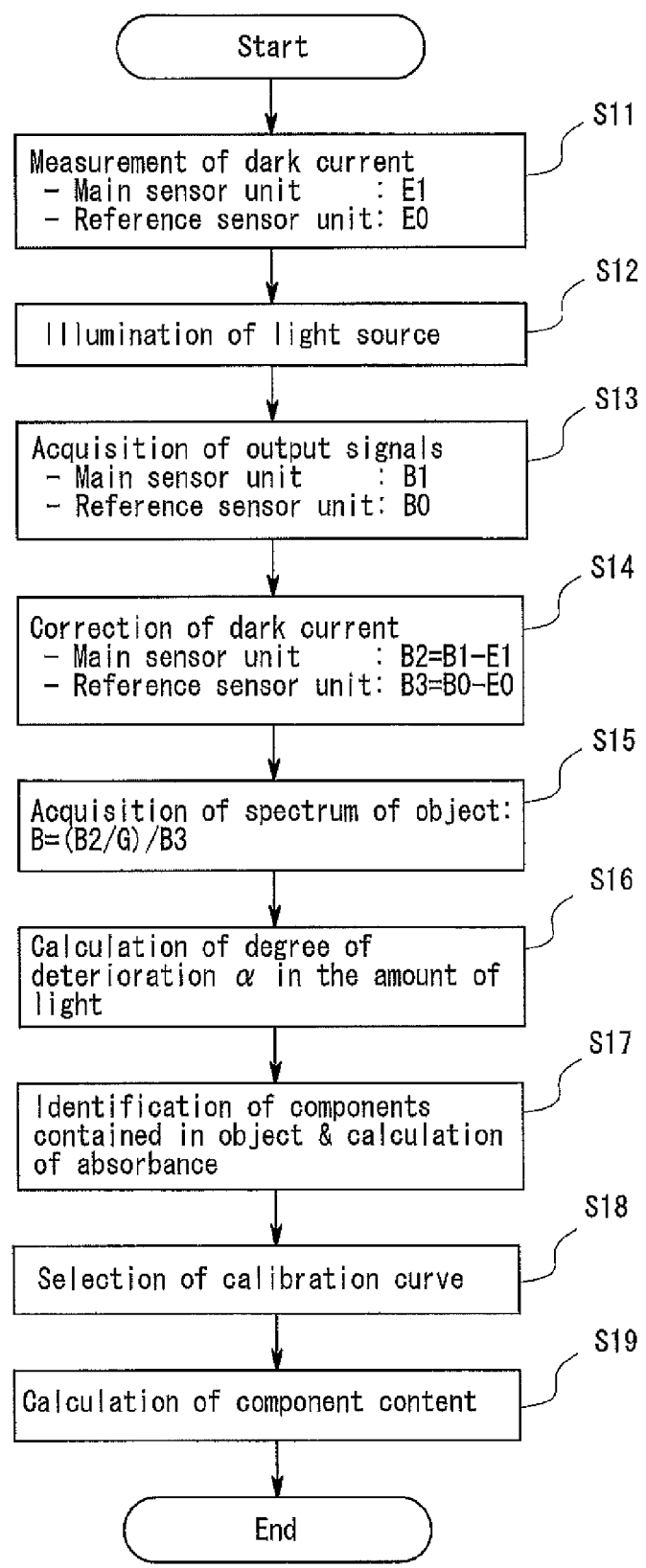
FIG. 7 is a flowchart showing operations of the analysis device in Embodiment 2 of the present invention.

As shown in FIG. 7, initially, the analysis unit 34 measures the dark current in the main sensor unit 20, and the dark current in the reference sensor unit 50 (step S11). Specifically, the analysis unit 34 measures output values $E1_1$-$E1_n$ of the output signals output by the light detector 23, and output values $E0_1$-$E0_n$ of the output signals output by the light detector 53, in a state in which the drive unit 33 has been caused to turn off the light source 11. Also, the analysis unit 31 is able to derive an average value Em1 of the output values $E1_1$-$E1_n$ and an average value Em0 of the output values $E0_1$-$E0_n$, and to user the average value Em1 and the average value Em0 in subsequent computations.

Also, step S11 does not need to be executed continuously with step S12 which will be described below, and the steps from step S12 onward may be executed repeatedly after step S11 has been executed once. That is, step S11 need only be executed once before execution of step S12. Also, there may be a time lag between execution of step S11 and execution of steps S12 onward.

Next, the analysis unit 34 causes the drive unit 33 to turn on the light source 11 (step S12). At this time, in the present Embodiment 2, as mentioned above, the drive unit 33 causes the light source 11 to continuously emit light. Light emitted from the light source 11 as a result of step S12 is split by the beam splitter 61, and one beam is incident on the main sensor unit 20 after being reflected by the object 40. The other beam is incident on the reference sensor unit 50 via the ND filter 61.

Next, the analysis unit 34 acquires the output signals from the main sensor unit 20 and the output signals from the reference sensor unit 50 (step S13). Specifically, the analysis unit 34 measures output values $B1_1$-$B1_n$ of the output signals output by the light detector 23, and output values $B0_1$-$B0_n$ of the output signals output by the light detector 53.

Next, the analysis unit 34 performs dark current correction on the output signals from the main sensor unit 20 and the output signals from the reference sensor unit 50 that were obtained at step S13 (step S14).

Specifically, at step S14, the analysis unit 31, with regard to the main sensor unit 20, subtracts the output values $E1_1$-$E1_n$ of dark current from the output values $B1_1$-$B1_n$ measured at step S13 and performs baseline correction, using the following Equation 5. In the following Equation 5, $B2_k$ denotes the output value of the main sensor unit 20 after correction. "k", similarly to Embodiment 1, denotes that the value was obtained from the k-th light receiving element, where $1 \le k \le n$.

$$B2_k = B1_k - E1_k \quad \text{Equation 5}$$

Similarly, at step S14, the analysis unit 31, with regard to the reference sensor unit 50, subtracts the output values $E0_1$-$E0_n$ of dark current from output value $B0_1$-$B0_n$ measured at step S13 and performs baseline correction, using the following Equation 6. In the following Equation 6, $B3_k$ denotes the output value of the reference sensor unit 50 after correction.

$$B3_k = B0_k - E0_k \quad \text{Equation 6}$$

Next, the analysis unit 34 acquires the spectrum of the object 40, using the baseline-corrected output values $B2_1$-$B2_n$ of the main sensor unit 20, and baseline-corrected output values $B3_1$-$B3_n$ of the reference sensor unit 50 (step S15). Specifically, the analysis unit 34 calculates diffusion intensities $B_1$-$B_n$ for each light receiving element 54 (each wavelength), using the following Equation 7. In the following Equation 7, G is a coefficient set as appropriate according to the light path or the like.

$$B_k = (B2_k/G)/B3_k \quad \text{Equation 7}$$

When the diffusion intensities $B_1$-$B_n$ calculated using the above Equation 7 are plotted on a coordinate system whose horizontal axis is wavelength and whose vertical axis is voltage, a graph similar to the graph 55 shown in FIG. 4 is also obtained in this case. That is, the diffusion intensities $B_1$-$B_n$ calculated using the above Equation 7 represent the spectrum of the object 40. Given that the light source 11 also irradiates light in the infrared region in the present Embodiment 2, as mentioned above, a spectrum in the infrared region is obtained.

Next, the analysis unit 34 calculates the degree of deterioration in the amount of light of the light source 11 (step S16). Specifically, in the present Embodiment 2, the analysis unit 34, first, derives the average value of the output values $B0_1$-$B0_n$ of the reference sensor unit 50 that were measured at step S13. The analysis unit 34 then calculates a ratio α of the derived average value and a preset reference value S (average value/reference value), for example, as the degree of deterioration. Note that the average value, maximum value or minimum value of the output values of signals output by the light receiving elements 54 of the reference sensor unit 50 when a new light source 11 is turned on for the first time, for example, can be used as the reference value S.

Next, the analysis unit 34 identifies components contained in the object 40 based on the spectrum obtained at step S15, by specifying the peak wavelength that appears in the spectrum, for example, and, furthermore, calculates the absorbance $A_\lambda$ from the value of the peak wavelength (step S17). In step S17, identification of the components contained in the object 40 is performed similarly to step S7 shown in FIG. 3 in Embodiment 1. That is, the analysis unit 34 applies the specified peak wavelength to an occurrence pattern stored in the storage unit 32, and identifies components contained in the object 40 from the result.

Also, in step S17, the analysis unit 34 calculates the absorbance $A_\lambda$ from the following Equation 8. Note that in the following Equation 8, j represents the light receiving element that outputs the peak value. Also, $1 \le j \le n$.

$$A_\lambda = -\log_{10}(B_j/\alpha) \qquad \text{Equation 8}$$

Next, the analysis unit 34 accesses the storage unit 32, and selects calibration curves (see FIGS. 5(a)-(c)) corresponding to the object 40, based on the identification result at step S17 (step S18). Step S18 is a similar step to step S8 shown in FIG. 3 in Embodiment 1.

Thereafter, the analysis unit 34 calculates the content (concentration) of the components contained in the object 40 by applying the absorbance $A_\lambda$ calculated at step S17 to the calibration curves selected at step S18 (step S19). Step S19 is a similar step to step S9 shown in FIG. 3 in Embodiment 1.

As mentioned above, according to the analysis device 2 in the present Embodiment 2, the component content of the object 40 can be calculated without acquiring the total reflection spectrum, different from Embodiment 1. Furthermore, the occurrence of an error in the case of causing the light source 11 to continuously emit light can also be suppressed.

In the present Embodiment 2, similarly to Embodiment 1, it is possible to specify components contained in the object 40 and suitable calibration curves, and to perform component analysis of various objects. Also, since the optical system required in order to perform component analysis has a simple configuration, an increase in device size is suppressed.

Note that in the present Embodiment 2, since the spectral filter 22 and the spectral filter 52 are configured so that the wavelength of incident light differs for each light receiving element, the analysis unit 34 performs arithmetic operations on output values for each light receiving element. However, the present invention is not limited to this example. For example, the spectral filter 22 and the spectral filter 52 may be configured so that the wavelength of the incident light differs for each group constituted by two or more light receiving elements. In this case, the analysis unit 34 calculates the average value of output values for each group, and performs the abovementioned arithmetic operations using the obtained average values.

Embodiment 3

Figure 8:
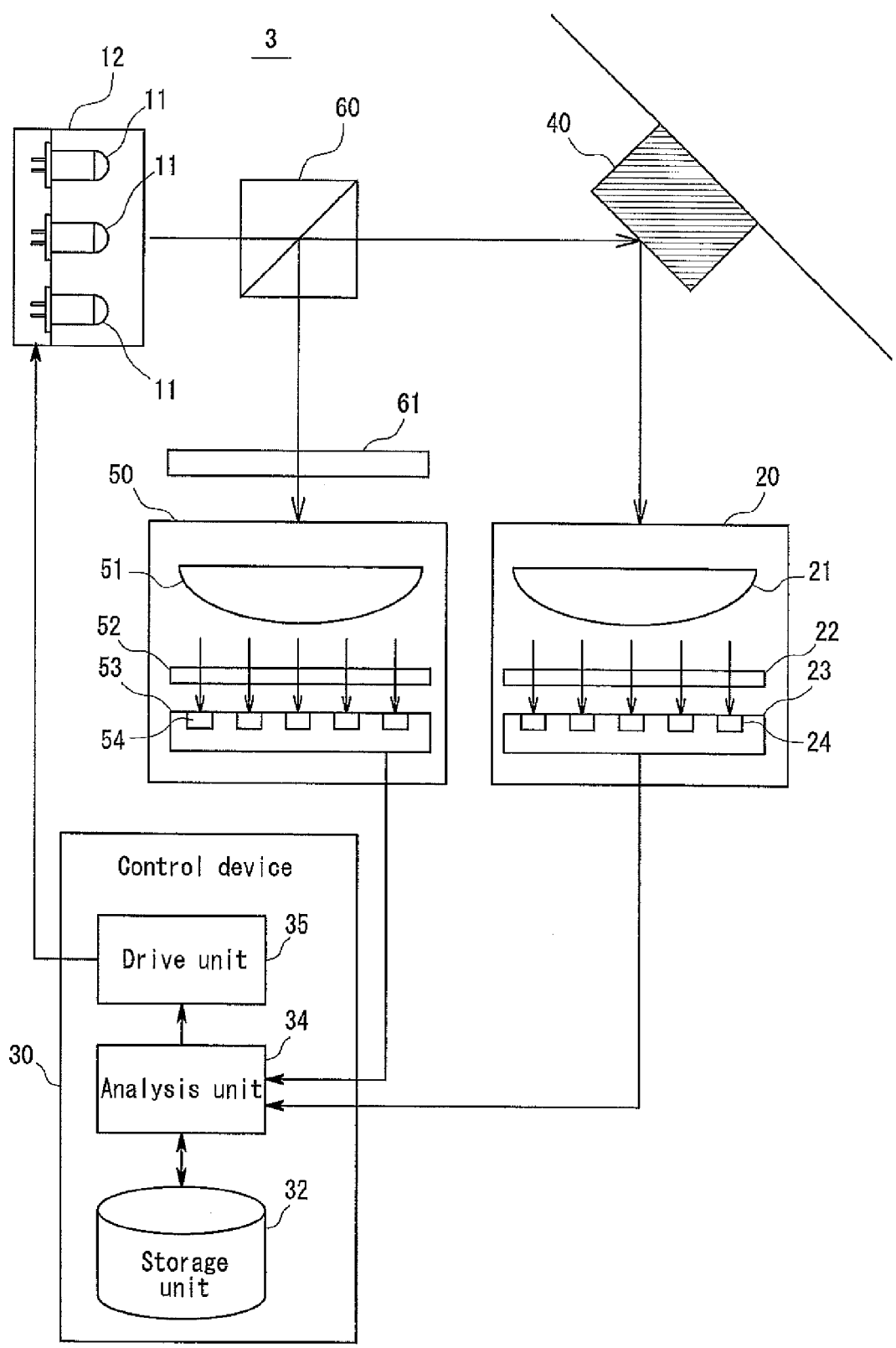
FIG. 8 is a configuration diagram showing a schematic configuration of an analysis device in Embodiment 3 of the present invention.

Next an analysis device in Embodiment 3 of the present invention will be described, with reference to FIG. 8. FIG. 8 is a configuration diagram showing a schematic configuration of the analysis device in Embodiment 3 of the present invention. As shown in FIG. 8, in the present Embodiment 3, the analysis device 3 is constituted similarly to the analysis device 2 in Embodiment 2 shown in FIG. 6, except for a light emitting unit 12 and a drive unit 35. Hereinafter, description will focus on the differences from Embodiment 2.

As shown in FIG. 8, in the present Embodiment 3, the light emitting unit 12, different from the light emitting unit 10 shown in FIG. 1 and FIG. 6, is provided with a plurality of light sources 11. Also, in the present Embodiment 3, when the drive unit 35 of the control device 30 turns on the light sources 11, the light sources 11 are turned on alternately, and light is continuously emitted from the light emitting unit 12.

In this way, in the present Embodiment 3, light can be quasi-continuously emitted from the light emitting unit 12, without each light source 11 being continuously turned on. The analysis device 3 thus operates in order of steps S11 to S15 and then S17 to S19 shown in FIG. 7, excluding step S16. In the present Embodiment 3, since the degree of deterioration does not need to be calculated for each light source 11, the load on the analysis unit 34 is reduced. Also, because light can be caused to be continuously incident on the main sensor unit 20 and the reference sensor unit 50, improvement in calculation accuracy is also achieved as compared with the case where pulsed light is incident.

Although the invention of this application was described heretofore with reference to the embodiments, the invention of this application is not limited to the above embodiments. Those skilled in the art will appreciate that various modifications can be made to the configurations and details of the invention of this application without departing from the scope of the invention of this application.

This application is based upon and claims the benefit of priority of the prior Japanese Patent Application No. 2010-067808, filed on Mar. 24, 2010, the entire contents of which are incorporated herein by reference.

An analysis device in the invention of this application has the following features.

(1) An analysis device for analyzing components contained in an object includes a light emitting unit that irradiates the object with light, a transmissive spectral filter, a light detector having a plurality of light receiving elements, and an analysis unit, the spectral filter including a substrate having light transmissivity and being disposed on a light path of the light after being reflected by the object or the light after passing through the object, a plurality of raised portions formed with a metal material on one surface of the substrate, and a metal oxide film formed using a metal oxide material having a higher refractive index than the metal material, so as to cover the plurality of raised portions and the one surface of the substrate, the plurality of raised portions being disposed such that the metal oxide film existing between adjacent raised portions serves as a diffraction grating and the raised portions serve as a waveguide, at least one of a grating pitch of the diffraction grating, a height of the raised portions, and a thickness of the metal oxide film is set to a different value for each portion of the spectral filter, such that a wavelength of light that passes through the spectral filter changes for each of the portions, the light detector is disposed such that each of the plurality of light receiving elements receives light that passes through the spectral filter, and the analysis unit acquires a spectrum of the object from output signals respectively output by the plurality of light receiving elements.

(2) In the analysis device according to (1) above, the analysis unit identifies a component contained in the object from the acquired spectrum, selects a calibration curve corresponding to the identified component from a plurality of calibration curves prepared in advance, and calculates a content of the component using the selected calibration curve.

(3) In the analysis device according to (1) above, that the light emitting unit irradiates the object with light intermittently.

(4) In the analysis device according to (1) above, the light emitting unit is provided with a plurality of light emitting elements, and irradiates the object with light continuously by causing one or two or more of the light emitting elements to emit light alternately.

(5) In the analysis device according to (1) above, the analysis device further includes a beam splitter that splits light irradiated by the light emitting unit, and a reference sensor unit that receives light split by the beam splitter and outputs a reference signal, the beam splitter is disposed between the light emitting unit and the object, the reference sensor unit includes an attenuating filter, a second spectral filter that is the same as the spectral filter, and a second light detector that is the same as the light detector, the attenuating filter, the second spectral filter and the second light detector are disposed such that the light split by the beam splitter is incident in order of the attenuating filter, the second spectral filter and the second light detector, a plurality of light receiving elements of the second light detector output signals according to incident light, and the analysis unit corrects the output signal of each of the plurality of light receiving elements of the light detector based on the signals from the second light detector.

(6) In the analysis device according to (1) above, the grating pitch of the diffraction grating is formed for each portion of the spectral filter, so as to be shorter than the wavelength of light required to pass through the portion.

(7) In the analysis device according to (1) above, a material of the substrate includes silicon oxide, the metal material includes gold (Au), and the metal oxide material includes titanium oxide.

(8) In the analysis device according to (1) above, the plurality of raised portions are each formed in a rectangular column shape, and are disposed in a matrix.

(9) In the analysis device according to (1) above, the light detector is a solid-state imaging device having a semiconductor substrate on which the plurality of light receiving elements are formed in a matrix.

INDUSTRIAL APPLICABILITY

According to an analysis device of the present invention, as described above, analysis of a wide variety of components can be handled, while suppressing an increase in device size. An analysis device of the present invention is useful in a variety of analysis that targets fruit, vegetables and other foodstuffs, chemical substances, various body fluids typified by blood extracted from living organisms, and the like.

LIST OF REFERENCE NUMERALS

1 Analysis device (Embodiment 1)
2 Analysis device (Embodiment 2)
3 Analysis device (Embodiment 3)
10 Light emitting unit
11 Light source
12 Light emitting unit
20 Main sensor unit
21 Lens
22 Spectral filter
22a Substrate
22b Raised portion
22c Metal oxide film
23 Light detector
24 Light receiving element
30 Control device
31 Analysis unit
32 Storage unit
33 Drive unit
34 Analysis unit
35 Drive unit
40 Object
50 Reference sensor unit
51 Lens
52 Spectral filter
53 Light detector
54 Light receiving element
60 Beam splitter
61 Neutral density filter

The invention claimed is:
1. An analysis device for analyzing components contained in an object, the analysis device comprising:
   a light emitting unit that irradiates the object with light;
   a transmissive spectral filter;
   a light detector comprising a plurality of light receiving elements;
   an analysis unit,
      wherein the spectral filter includes:
         a substrate having light transmissivity and being disposed on a light path of the light after being reflected by the object or the light after passing through the object;
         a plurality of raised portions formed with a metal material on one surface of the substrate; and
         a metal oxide film comprising a metal oxide material having a higher refractive index than the metal material, so as to cover the plurality of raised portions and the one surface of the substrate,
      wherein the plurality of raised portions are disposed such that the metal oxide film existing between adjacent raised portions serves as a diffraction grating, incident light that is incident on the raised portions propagating inside the raised portions as an evanescent wave,
      wherein at least one of a grating pitch of the diffraction grating, a height of the raised portions, and a thickness of the metal oxide film is set to a different value for each portion of the spectral filter, such that a wavelength of light that passes through the spectral filter changes for each of the portions,
      wherein the light detector is disposed such that each of the plurality of light receiving elements receives light that passes through the spectral filter,
      wherein the analysis unit acquires a spectrum of the object from output signals respectively output by the plurality of light receiving elements, identifies a component contained in the object from the acquired spectrum, selects a calibration curve corresponding to the identified component from a plurality of calibration curves prepared in advance, and calculates a content of the component using the selected calibration curve, and
      wherein the material of the substrate includes silicon oxide, and the metal oxide material of the metal oxide film includes titanium oxide ($TiO_2$);
   a beam splitter that splits light irradiated by the light emitting unit; and
   a reference sensor unit that receives the light split by the beam splitter and outputs a reference signal, wherein the beam splitter is disposed between the light emitting unit and the object, wherein the reference sensor unit includes:
- an attenuating filter,
- a second spectral filter that is the same as the spectral filter; and
- a second light detector that is the same as the light-detector, wherein the attenuating filter, the second spectral filter, and the second light detector are disposed such that the light split by the beam splitter is incident in order of the attenuating filter, the second spectral filter, and the second light detector, wherein a plurality of light receiving elements of the second light detector output signals according to incident light, and wherein the analysis unit corrects the output signal of each of the plurality of light receiving elements of the light detector based on the signals from the second light detector.

2. The analysis device according to claim 1, wherein the light emitting unit irradiates the object with light intermittently.

3. The analysis device according to claim 1, wherein the light emitting unit is provided with a plurality of light emitting elements, and irradiates the object with light continuously by causing one or two or more of the light emitting elements to emit light alternately.

4. The analysis device according to claim 1, wherein the grating pitch of the diffraction grating is formed for each portion of the spectral filter, so as to be shorter than the wavelength of light required to pass through the portion.

5. The analysis device according to claim 1, wherein the metal material includes gold (Au).

6. The analysis device according to claim 1, wherein the plurality of raised portions are each formed in a rectangular column shape, and are disposed in a matrix.

7. The analysis device according to claim 1, wherein the light detector comprises a solid-state imaging device including a semiconductor substrate on which the plurality of light receiving elements are formed in a matrix.

8. The analysis device according to claim 2, wherein the grating pitch of the diffraction grating is formed for each portion of the spectral filter, so as to be shorter than the wavelength of light required to pass through the portion.

9. The analysis device according to claim 3, wherein the grating pitch of the diffraction grating is formed for each portion of the spectral filter, so as to be shorter than the wavelength of light required to pass through the portion.

10. The analysis device according to claim 2, wherein the metal material includes gold (Au).

11. The analysis device according to claim 1, wherein light of a set frequency, among types of light included in the incident light, reaches the substrate and is transmitted through the substrate.

12. The analysis device according to claim 1, wherein only light of a set frequency, among types of light included in the incident light, reaches the substrate and is transmitted through the substrate.

13. The analysis device according to claim 1, wherein the incident light, which is incident on the spectral filter from another side of the light detector, is incident on the raised portion from the metal oxide film.

14. The analysis device according to claim 1, wherein the analysis unit is configured to calculate the content of the component by deriving absorbance from the acquired spectrum of the object and applying the derived absorbance to the selected calibration curve.

* * * * *